(12) United States Patent
Cosman

(10) Patent No.: US 6,662,036 B2
(45) Date of Patent: Dec. 9, 2003

(54) SURGICAL POSITIONING SYSTEM

(75) Inventor: Eric R. Cosman, Belmont, MA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 10/208,283

(22) Filed: Jul. 29, 2002

(65) Prior Publication Data

US 2002/0188194 A1 Dec. 12, 2002

Related U.S. Application Data

(63) Continuation of application No. 10/043,584, filed on Jan. 10, 2002, now abandoned, which is a continuation of application No. 08/980,572, filed on Dec. 1, 1997, now Pat. No. 6,405,072, which is a continuation-in-part of application No. 08/482,213, filed on Jun. 7, 1995, now Pat. No. 5,848,967, which is a continuation of application No. 08/299,987, filed on Sep. 1, 1994, now abandoned, which is a continuation of application No. 08/047,879, filed on Apr. 15, 1993, now abandoned, which is a continuation of application No. 07/941,863, filed on Sep. 8, 1992, now abandoned, which is a continuation of application No. 07/647,463, filed on Jan. 28, 1991, now abandoned.

(51) Int. Cl.[7] .................................................. A61B 5/00
(52) U.S. Cl. ........................ 600/411; 600/414; 600/417; 600/426; 600/427; 600/429; 600/439; 606/130
(58) Field of Search ................................ 600/425–427, 600/429, 414, 417, 411; 606/130

(56) References Cited

U.S. PATENT DOCUMENTS 3,821,469 A 6/1974 Whetsone et al.

(List continued on next page.)

FOREIGN PATENT DOCUMENTS

| EP | 0 018 166 | 10/1980 |
|----|-----------|---------|
| EP | 0 062 941 | 10/1982 |
| EP | 0 326 768 | 8/1989 |
| EP | 0 359 773 | 3/1990 |
| FR | 2417-970 | 10/1979 |
| GB | 2 094 590 | 9/1982 |
| WO | WO 90/05494 | 5/1990 |
| WO | WO 91/07726 | 5/1991 |

OTHER PUBLICATIONS

Kosugi, Yukio et al, "An Articulated Neurosurgical Navigation System Using MRI and CT Images", IEEE *Transactions on Biomedical Engineering*, vol. 35, No. 2, pp. 147–152, Feb. 1988.

(List continued on next page.)

*Primary Examiner*—Ruth S. Smith

(57) ABSTRACT

A system for positioning and repositioning a portion of a patient's body with respect to a treatment or imaging machine includes multiple cameras to view the body and the machine. Index markers are identified and located by the cameras in 3D space. In one embodiment, such index markers are in a determinable relationship to analogous markers used during previous image scanning of the patient. Anatomical targets determined from image scanning can be located relative to reference positions associated with the treatment of diagnostic machine. Several forms of camera, index markers, methods and systems accommodate different clinical uses. X-ray imaging of the patient further refines anatomical target positioning relative to the treatment of diagnostic imaging reference point. Movements of the patient based on comparative analysis of imaging determined anatomical targets relative to reference points on treatment or diagnostic apparatus are controlled by the system and process of the invention.

7 Claims, 8 Drawing Sheets

U.S. PATENT DOCUMENTS

| | | |
|---|---|---|
| 3,983,474 A | 9/1976 | Kuipers |
| 4,058,114 A | 11/1977 | Soldner |
| 4,068,156 A | 1/1978 | Johnson et al. |
| 4,068,556 A | 1/1978 | Foley |
| 4,182,312 A | 1/1980 | Mushabac |
| 4,262,306 A | 4/1981 | Renner |
| 4,341,220 A | 7/1982 | Perry |
| 4,358,856 A | 11/1982 | Stivender et al. |
| 4,407,298 A | 10/1983 | Lentz et al. |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,571,834 A | 2/1986 | Fraser et al. |
| 4,583,538 A | 4/1986 | Onik et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Shelden et al. |
| 4,645,343 A | 2/1987 | Stockdale et al. |
| 4,651,732 A | 3/1987 | Frederick |
| 4,659,971 A | 4/1987 | Suzuki et al. |
| 4,660,970 A | 4/1987 | Ferrano |
| 4,674,057 A | 6/1987 | Caughman et al. |
| 4,686,997 A | 8/1987 | Oloff et al. |
| 4,698,777 A | 10/1987 | Toyoda et al. |
| 4,701,049 A | 10/1987 | Beckman et al. |
| 4,701,407 A | 10/1987 | Appel |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,722,056 A | 1/1988 | Roberts et al. |
| 4,723,544 A | 2/1988 | Moore et al. |
| 4,733,661 A | 3/1988 | Palestrant |
| 4,733,969 A | 3/1988 | Case et al. |
| 4,737,032 A | 4/1988 | Addleman et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Barlett et al. |
| 4,753,528 A | 6/1988 | Hines et al. |
| 4,761,072 A | 8/1988 | Pryor |
| 4,762,016 A | 8/1988 | Stoughton et al. |
| 4,764,016 A | 8/1988 | Johansson |
| 4,776,749 A | 10/1988 | Wanzenberg et al. |
| 4,779,212 A | 10/1988 | Levy |
| 4,791,934 A | 12/1988 | Brunnett |
| 4,794,262 A | 12/1988 | Sato et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,841,967 A | 6/1989 | Chang et al. |
| 4,875,478 A | 10/1989 | Chen |
| 4,896,673 A | 1/1990 | Rose et al. |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,954,043 A | 9/1990 | Yoshida et al. |
| 4,955,891 A | 9/1990 | Carol |
| 4,961,422 A | 10/1990 | Marchosky et al. |
| 4,991,579 A | 2/1991 | Allen |
| 5,016,639 A | 5/1991 | Allen |
| 5,017,139 A | 5/1991 | Mushabac |
| 5,027,818 A | 7/1991 | Bova et al. |
| 5,047,036 A | 9/1991 | Koutrouvelis |
| 5,050,608 A | 9/1991 | Watanabe et al. |
| 5,078,140 A | 1/1992 | Kwoh |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,836 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,186,174 A | 2/1993 | Schlöndorff et al. |
| 5,193,106 A | 3/1993 | DeSena |
| 5,197,476 A | 3/1993 | Nowacki et al. |
| 5,207,223 A | 5/1993 | Adler |
| 5,211,164 A | 5/1993 | Allen |
| 5,224,049 A | 6/1993 | Mushabac |
| 5,230,338 A | 7/1993 | Allen et al. |
| 5,251,127 A | 10/1993 | Raab |
| 5,305,203 A | 4/1994 | Raab |
| 5,315,630 A | 5/1994 | Sturm et al. |
| 5,383,454 A | 1/1995 | Bucholz |
| 5,389,101 A | 2/1995 | Heilbrun et al. |
| 5,617,857 A | 4/1997 | Chader |
| 5,622,170 A | 4/1997 | Schulz |
| 5,662,111 A | 9/1997 | Cosman |
| 5,755,725 A | 5/1998 | Druais |
| 5,847,967 A | 12/1998 | Asao |
| 5,848,967 A | 12/1998 | Cosman |
| 5,947,981 A | 9/1999 | Cosman |
| 6,006,126 A | 12/1999 | Cosman |
| 6,143,003 A | 11/2000 | Cosman |
| 6,275,725 B1 | 8/2001 | Cosman |
| 6,351,661 B1 | 2/2002 | Cosman |
| 6,405,072 B1 | 6/2002 | Cosman |

OTHER PUBLICATIONS

Adams, Ludwig et al., "Computer–Assisted Surgery", IEEE *Computer Graphics & Applications*, pp. 43–51, May 1990.

Wolfe, William L., et al., "Image Trackers", *The Infrared Handbook*, Environmental Research Institute of Michigan for the Office of Naval Research, 1978, pp. 22–63 –22–67 and 22–74 –22–77 (Chapter from a Book).

Castleman, Kenneth R., "Stereometric Ranging", *Digital Image Processing*, Prentice–Hall, Inc., Englewood Cliffs, New Jersey 1979, pp. 364–369 (Chapter from a Book).

Foley, James D., et al., "Geometrical Transformations", *Fundamentals of Interactive Computer Graphics*, Second Edition, Addison–Wesley Publishing Company, 1984, Chapter 7, pp. 245–266 (Chapter from a Book).

Newman and Sproull, "Moving Parts Of An Image", *Principles of Interactive Computer Graphic*, McGraw–Hill Book Company, 1979, Section 17.3, p. 254 (Section from a Book).

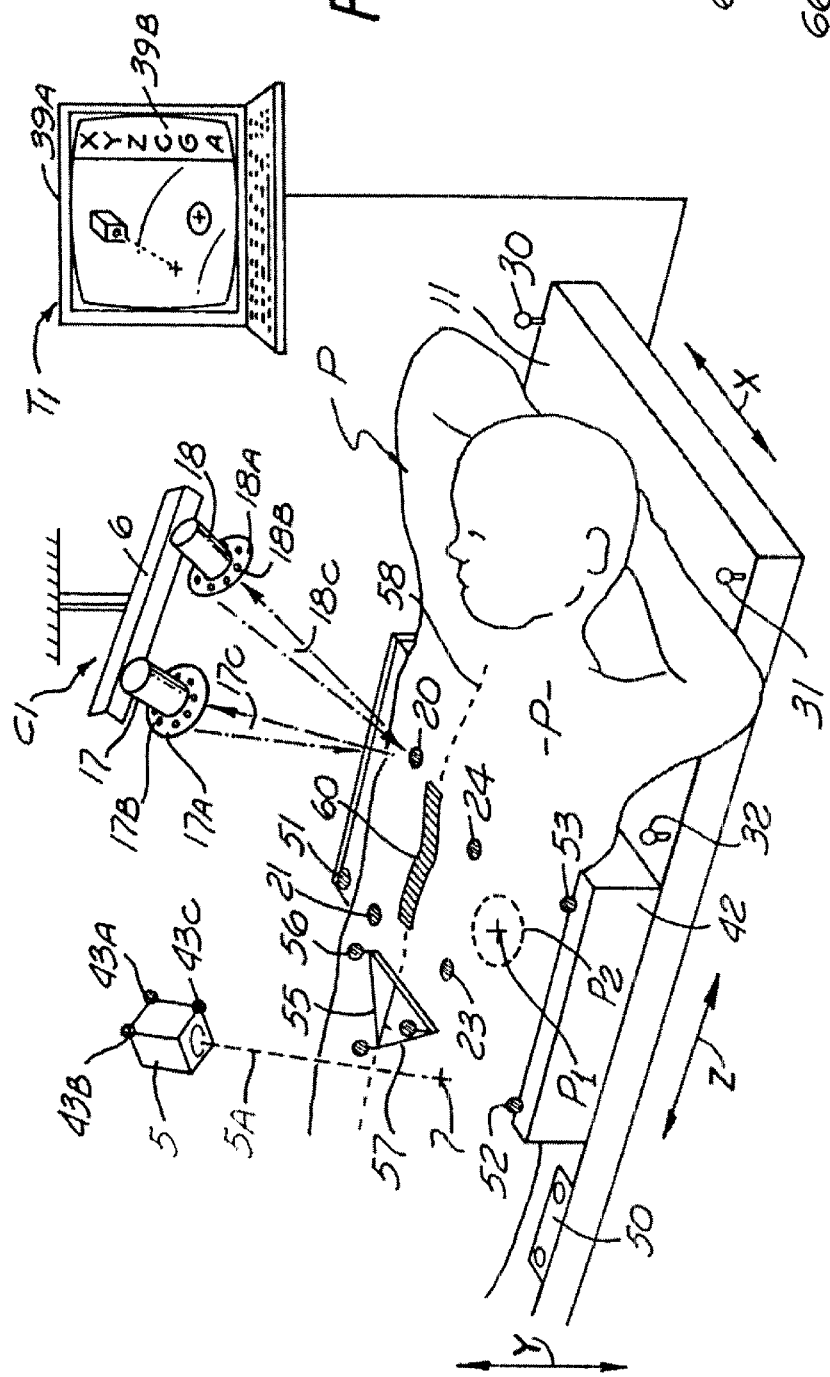
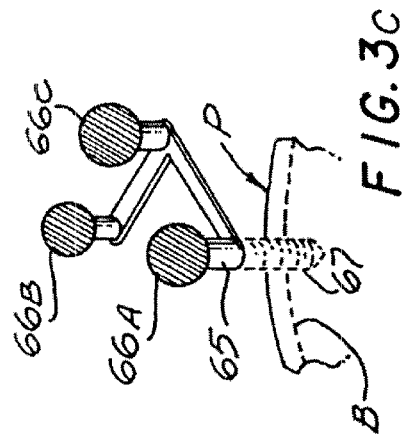
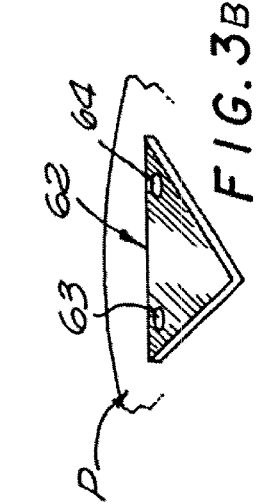
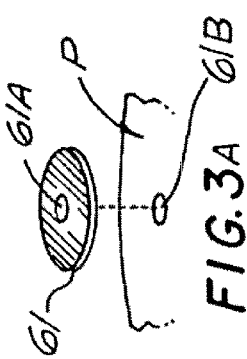
FIG. 2
FIG. 3C
FIG. 3B
FIG. 3A

SURGICAL POSITIONING SYSTEM

This application is a continuation of U.S. application Ser. No. 10/043,584, filed on Jan. 10, 2002, now abandoned which is a continuation of U.S. application Ser. No. 08/980,572, filed on Dec. 1, 1997 now U.S. Pat. No. 6,405,072, which is a continuation in part of U.S. application Ser. No. 08/482,213, filed Jun. 7, 1995 by Eric R. Cosman for "An Optically Coupled Frameless Stereotactic Space Probe," now U.S. Pat. No. 5,848,967 which is a continuation of Ser. No. 08/299,987, filed Sep. 1, 1994 by Eric R. Cosman for "An Optically Coupled Frameless Stereotactic Space Probe," now abandoned, which is a continuation of Ser. No. 08/047,879, filed Apr. 15, 1993 for "An Optically Coupled Frameless Stereotactic Space Probe," now abandoned, which is a continuation of Ser. No. 07/941,863, filed Sep. 8, 1992 by Eric R. Cosman for "An Optically Coupled Frameless Stereotactic Space Probe," now abandoned, which is a continuation of Ser. No. 07/647,463, filed Jan. 28, 1991 by Eric R. Cosman for "An Optically Coupled Frameless Stereotactic Space Probe," now abandoned.

BACKGROUND AND SUMMARY OF THE INVENTION

Frameless stereotaxy is widely used in the field of neurosurgery. It involves the quantitative determination of anatomical positions based on scan data taken from a CT, MRI or other scanning procedures to obtain three-dimensional scan data. Typically, the image scan data is placed in a computer to provide a three-dimensional database that may be variously used to provide graphic information. Essentially, such information is useful in surgical procedures and enables viewing a patient's anatomy in a graphics display.

The use of stereotactic head frames is commonplace, for example, see U.S. Pat. No. 4,608,977 issued Sep. 2, 1986 and entitled, System Using Computed Tomography as for Selective Body Treatment. Such structures employ a head fixation device typically with some form of indexing to acquire referenced data representative of scan slices through the head. The scan data so acquired is quantified relative to the head frame to identify individual slices. Three-dimensional scan data has been employed to relate positions in a patient's anatomy to other structures so as to provide a composite graphics display. For example, a space pointer (analogous to a pencil) might be directed at a patient's anatomy and its position quantified relative to the stereotactic scan data. The space pointer might be oriented to point at an anatomical target and so displayed using computer graphics techniques. Such apparatus has been proposed, using an articulated space pointer with a mechanical linkage. In that regard, see an article entitled "An Articulated Neurosurgical Navigational System Using MRI and CT Images," IEEE Transactions on Biomedical Engineering, Volume 35, No. 2, February 1988 (Kosugi, et al.) incorporated by reference herein.

Further to the above considerations, the need for relating external treatment apparatus to a specific target arises in several aspects. For example, the need arises in relation to the treatment of internal anatomical targets, specifically to position and maintain such targets with respect to a beam or isocenter of a linear accelerator (LINAC) X-ray treatment machine. Thus, a need exists for methods of aligning beams, such as from a LINAC machine, to impact specific targets.

Generally, in accordance herewith, an optical camera apparatus functions in cooperation with a LINAC machine and a computer to enable treatment of a patient with a beam that is positioned and maintained on a specific target in a patient's body. In an embodiment, the camera system is located in a known position with regard to the LINAC machine and to detect index markers at specific locations on a patient's body. The markers employed during image scanning processes correlate to reference points for the scan data. Thus, by correlation, anatomical targets in the body, identified in the image scan data are effectively positioned with respect to the treatment beam from the LINAC machine identified by camera data. Essentially, data accumulation, transformation and processing operations serve to correlate scan data with camera data and thereby enable the desired positional relationships for patient treatment as well as providing an effective graphics display.

BRIEF DESCRIPTION OF THE DRAWINGS

In the drawings, which constitute a part of the specification, exemplary embodiments exhibiting various objectives and features hereof are set forth. Specifically:

FIG. 2 is a perspective view of components somewhat similar to those of FIG. 1 shown in more or less detail for further explanations;

FIGS. 3A, 3B and 3C are perspective views showing index markers set in accordance with the present invention;

DESCRIPTION OF THE ILLUSTRATIVE EMBODIMENTS

The following embodiments illustrate and exemplify the present invention and concepts thereof, yet in that regard, they are deemed to afford the best embodiments for purposes of disclosure and to provide a basis for the claims herein which define the scope of the present invention.

Figure 1:
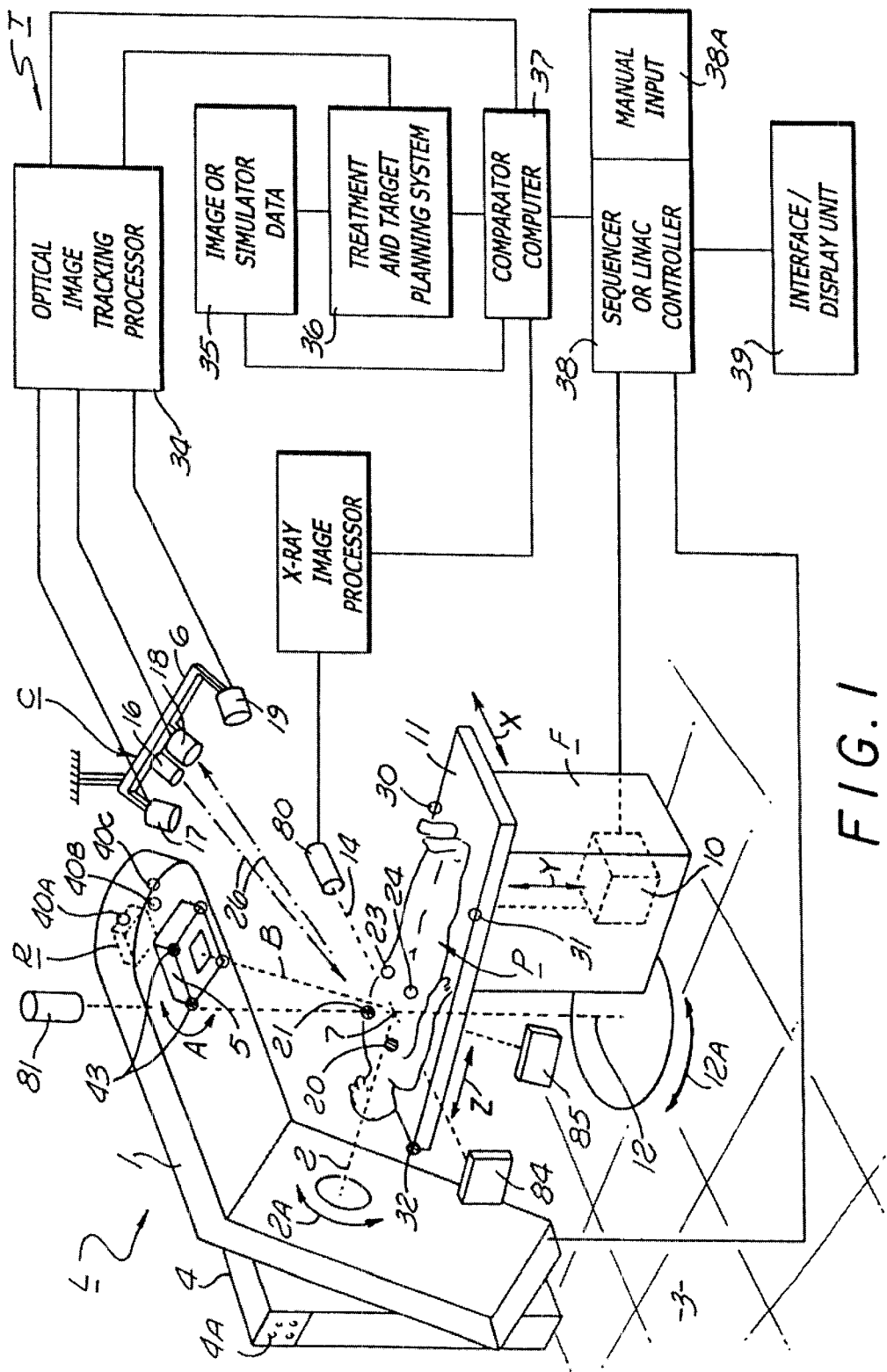
FIG. 1 is a perspective and diagrammatic view of a composite system in accordance with the present invention shown with reference to a patient.

Generally, the embodiment of FIG. 1 accomplishes optical location and/or X-ray location of a patient's anatomy for treatment. A linear accelerator (LINAC) X-ray radiation therapy machine, generally located at L (FIG. 1 upper left) provides a beam B (generally radiation with an isocenter) for treating a patient P (shown reclining on a platform or couch F). Typically, the beam B has a principal axis that coincides at a specific location (isocenter) and is positioned at a target in or on the patient P.

Basically, scan data is stored to specify the location of a target in a patient's body, generally defined in three-dimensional scan space (as slice data) with respect to references. The scan data is stored in a treatment processing system T which receives further data from a camera system C. Specifically the camera system C senses the instant position of the patient P and the beam B (in camera space) on the basis of marker locations on the patient P and the machine L. By using similar or related reference locations, scan space and camera space are correlated and the data is transformed to a common coordinate space. Accordingly, the beam B is related and displayed with respect to the patient P. Consequently, the beam B can be positioned and maintained to collimate at the desired target. Note that both the machine L and a patient-supporting couch F are moveable to accomplish and maintain desired positional relationships between the beam B and the patient P as described in greater detail below.

The LINAC machine L is mounted on a floor 3 and includes a gantry 1 which rotates about a horizontal axis 2, the angle of rotation being indicated by a double-ended arrow 2A. The gantry 1 is thus rotatably supported on a floor-mounted column or support structure 4 which includes a panel 4A for direct manual control. Control also may be provided from the treatment processing system T.

Remote from the support structure 4, the gantry 1 carries a radiation source R (shown in phantom) somewhat aligned with a collimator 5 which shapes the X-ray radiation from the source R to pass generally along the axis as indicated for the beam B. Well known structures may be employed as the radiation source R and the collimator 5. Specifically, the collimator 5 may be a multileaf, miniature multileaf, circular collimator, cut block, or other type of X-ray aperture. Typical LINAC machines, as currently known, could be used for the LINAC machine L operating to establish an isocenter point 7 (shown at the abdomen of the patient P) which point 7 is the convergence point of the central X-ray radiation (beam B for representation) and lies on the axis 2 of rotation.

As indicated above, the patient P lies on the couch F and is specifically shown reclining on a couch top 11. The couch top 11 is movable; that is it can be displaced in Cartesian translations as indicated by double-ended arrows X, Y and Z. Such displacements are accomplished by a mechanism 10, shown in phantom within the couch F. Direct manual control is afforded by the panel 4A with data control from the treatment processing system T. Note that the couch F also rotates about a vertical axis 12 (mechanical linkage) as indicated by a double-ended arrow 12A. A third orthogal axis 14 (patient lateral) is indicated to pass through the isocenter point 7 as will be described in detail below.

The camera system C comprises three cameras 17, 18 and 19 which may take the form of well known video cameras, infrared filtered cameras, linear CCD cameras (with either infrared or n-infrared sensitivity) or other cameras of acceptable design to resolve the contents of a space. The cameras 17, 18 and 19 are fixed on a frame 6 along with a light source 16, and are oriented to view the treatment space or field of the couch F, the gantry 1 and the patient P. Thus, the camera system C senses the contents of a volume occupied by the above-described elements. Additional cameras may be located in other positions within the treatment room viz. attached to the ceilings or walls.

Recognizing that various forms of markers can be used, if the index markers are of the reflecting type, a light source 16 (infrared) may be used to produce reflected light as indicated by dash line arrows 26. Although the light source 16 may not always be necessary, it can enhance the signal-to-noise ratio of the reflected light from the index markers as related to background. Note that for the same purpose additional similar light sources could be fixed on the frame 6, for example, near the cameras 17 and 19.

In operation, the camera system C senses several markers that indicate specific reference locations or index points. Specifically, the index points are sensed as indicated by markers 20, 21, 23 and 24 which are on the patient P, located, for example, on or near the patient's skin. As indicated, the markers 20, 21, 23 and 24 may take a variety of forms, for example, LED emitters, reflectors of light, reflecting spheres, reflecting dots or various other devices that can be tracked by the camera system C in three-dimensional space. Also, radiopaque circles can be adhered to the skin at points identified as by a tatoo or ink mark. Also, reflective markers can be placed precisely on tatoos or ink marks on the patient's skin.

The index markers 20, 21, 23 and 24 provide references for transforming image scan data (initially stored) to the coordinate space of the LINAC machine L, as sensed by the camera system C. That is, three-dimensional scan data taken during a preliminary procedure is stored in the treatment processing system T and is correlated to data provided from the camera system C by using common points as may be defined by the markers 20, 21, 23 and 24. The combined data accommodates the desired position and orientation of the couch F and/or the orientation and collimation of the beam B to impact the desired target in the subject patient P. The control operation is disclosed in greater detail below along with the correlation of data to provide a composite display relating the patient P to the treatment structure of FIG. 1.

Regarding the camera system C, the individual optical cameras 17, 18 and 19 essentially "look" at the position and orientation of the patient P, that is, viewing the volume containing the patient P and the apparatus as explained above. The markers 20, 21, 23, and 24 can be "seen" by the cameras to track marker positions relative to the isocenter point 7 and the beam B. By way of a disclosing reference, see U.S. Pat. No. 5,446,548, entitled "Patient Positioning and Monitoring System", L. H. Gerig and S. F. El-Hakim, issued Aug. 29, 1995; as well as an operating system identified as the OTS Optical Tracking System produced by Radionics, Inc. of Burlington, Mass., or a Motion Tracking System available from Oxford Metronics, Oxford, England.

As indicated, the optical signal outputs from the cameras 17, 18 and 19 are supplied to an optical image tracking processor 34 (FIG. 1, upper right) as well known in the field. In the operation of the processor 34, the individual camera data signals are translated into three-dimensional position data (in the camera coordinate space) related to objects in the cameras' collective field of view and including the identifying index markers 20, 21, 23 and 24. The resulting positional data defines the position of the patient P relative to objects in the field of view of the camera system C (in camera coordinate space).

Another set of markers, 30, 31 and 32 are attached to the couch F, shown variously disposed on the couch top 11. The markers 30, 31 and 32 also are detected by the camera system C to determine the orientation of the couch F relative to the camera system C. Thus, by using outputs from the camera system C, the processor 34 also provides data indicating the position of the couch F in camera space. Utilizing such data, the processor 34 functions with other components of the treatment processing system T to coordinate data and accomplish the functions as described above. Other components of the treatment processing system T include an imager 35, a treatment and planning system 36, a comparator/computer 37, a controller 38 and an interface display unit 39. The detailed operation of the treatment processing system T is treated below.

Still another set of index markers 40A, 40B and 40C is fixed on the gantry 1, also to indicate positions in camera space. Furthermore, markers 43 are fixed on the collimator 5 (end of the gantry 1) specifically to enable three-dimensional tracking of the gantry and the beam B relative to the patient P and the couch F. Thus, the camera system C provides data to coordinate the treatment machine L, the beam B relative to the patient P, aligning an anatomical target with the beam B at the isocenter point 7, or other focus of radiation.

Recapitulating to some extent, it will be understood that as explained above, during an initial procedure, scan data is taken from the patient, as by a CT or MRI scanner and stored in the imager 35. In accordance with one operating format, the scan data may comprise slice data, three-dimensionally representing a portion of the patient P in scan data space. Of course, scan data space is distinct from camera data space, compatibility being attained by translating to a common coordinate space. Transformations, using well-known techniques of the art, are accomplished by referencing certain markers, e.g., markers 20, 21, 23 and 24 which are located on the patient P and identify reference points in both space coordinates.

As indicated, during the scanning process, the positions of the index markers 20, 21, 23 and 24 on the patient P are determined in the coordinate space of the scanner (CT or MRI, scan space) employed to generate the image scan data. For example, for CT scanning, graphic reference markers can be radiopaque markers placed on the skin at positions indicated by index markers 20, 21, 23, and 24. They could be, for example, radiopaque circles stuck down to the skin at points where a tattoo or ink mark is made. Knowing the coordinates in the scan space, and the coordinate locations of anatomical objects relative to them (markers 20, 21, 23 and 24) the target sites to be radiated are determined relative to the index points defined by the markers 20, 21, 23 and 24. As indicated, image scan data for the index-marked positions is stored in the imager 35 or image data storage memory for use by the planning system 36 and the computer 37.

In the treatment planning computer 37, positions are determined for the markers 20, 21, 23 and 24, relative to the anatomy of the patient P and the selected internal anatomical targets. Accordingly, target coordinates within a volume are resolved in the scan data coordinate system.

The specific locations of the points identified by the markers 20, 21, 23 and 24 also are determined in camera space by the camera system C while the patient P is on the couch F. Thus, identical reference locations are provided in the two coordinate systems (scan and camera) enabling data transformations as well known in the computer graphics field. Specifically, the reference points are detected by the camera system C. This can be accomplished, for example, by placing LED's or reflective markers on the positions of the index markers as indicated by tatoo marks or ink spots used during the image scanning as described above. The marker positions are thereby determined in three-dimensional space relative to the camera system. Further, the marker positions on the patient's body are also determined relative to markers on the LINAC itself such as 30, 31, 32 on the couch 11 or 40A, 40B, and 40C on the gantry 1. Data from the camera system C is provided from the processor 34 to the comparator/computer 37 where the index marker locations are compared to marker positions determined from imaging data to accomplish a "best fit" as well known. Accordingly, the image data defining the patient is transformed to camera space. Thus, a target coordinate is determined from the treatment planning system 36 involving the explicit location of the target in relation to objects in the camera field of view including the collimator 5 and accordingly the beam B.

The three-dimensional position of the isocenter point 7 (in camera space) of the LINAC L is determined and controlled from a calibration procedure as described below. Thus, an internal selected target position as determined from the transformation into camera coordinate space is determined relative to the couch F, the gantry 1, the beam B and the isocenter point 7. Such information is provided to the controller 38 to position the gantry 1 and the couch F and thus, to control the treatment. The display unit 39 then dynamically indicates the positional relationships with a graphic image.

Specifically, controller 38 controls the angles and shapes of the radiation beam B determined by the treatment planning system 36. Again, beam approaches also can be transformed via the comparator/computer 37 to position the gantry collimator 7 and that of the couch F (actuated by the controller 38). The controller 38 also can incorporate structure to record and verify positional relationships including those of the beam B and the patient P as well as controlling the status of the beam B (on and off) and dose rates during treatment.

For an example of a standard controller 38 and treatment planning system 36 as may be used in the system, see the Mevatron Linac provided by Siemens Oncology Care Systems Inc., of Concord, Calif., as well as the product, XKnife Treatment Planning System available from Radionics, Inc. A typical display of relevant information at each point in a treatment process is indicated by an interface and the image of the display unit 39.

After determining the position of desired treatment target in the patient P using the coordinate space of the camera system C and also determining the relative position and distance of that target from the isocenter point 7, also in camera space, the couch F is moved to access the desired target with the isocenter point 7. In that configuration, the beam B is directed from the collimator 5 to the target. The process can be automated, with appropriate sequencing by the controller 38 for correctively driving the couch F. Accordingly, the beam B is maintained with the isocenter point 7 on the desired target.

The camera system C can monitor the process as described above and provide a feedback signal for automatically driving the couch F. Beam positions and dose rates measured in monitor units through the collimator 5 also can be preplanned and actuated either by manual-operator control 38A (panel 4A) or automatically through the controller 38.

If multiple targets or a broad target field are to be radiated, or if intensity modulation of beams is specified, the controller 38 can move sequentially to different target positions within a generalized target volume, for example, attaining sequential positions, defined in X, Y and Z coordinates as well as dose rates, all achieved to effect a desired pattern of radiation.

In a dynamic mode of the system, corrections may be provided for patient movement during treatment along with continual confirmation of the patient's body position relative to the LINAC machine. If there is respiratory body movement of the patient P, as would typically occur in the torso region, the tidal movement can be observed by the camera system C tracking the index markers 20, 21, 23 and 24. Synchronizing the radiation from the LINAC machine L can assure that the anatomical target is impacted by the beam 6 even though the patient's internal organs are moving. This too can be controlled by the controller 38 with feedback to the optical tracking processor 34 through the comparator 37. Consequently, the comparator 37 enables streamlining certain complex procedures and even routine procedures, as compared to standard current radiotherapy steps relying primarily on laser lights associated with a radiation machine and tatoo markings on the patient.

FIG. 2 is a fragmentary view showing certain components of the system of FIG. 1, whole or fragmented and generally bearing similar reference numerals, however, modified in some regards to illustrate other embodiments of the present invention. Note generally that the collimator 5 is representative of the LINAC machine L for treating the patient P positioned on the surface or top 11 of the couch 10. The entire processing system T1 of FIG. 2 may incorporate the elements described with reference to FIG. 1 and is embodied in a unit 39A embodying a graphics display.

A camera system C1 (FIG. 2) comprises two cameras, 17 18, that are stably secured (symbolically indicated), as to the ceiling of the treatment room. The cameras 17 and 18 are fitted with annular rings 17A and 18A, respectively, each containing a circular array of multiple light sources 17B and 18B respectively. The light sources 17B and 18B may be LED's (light emitting diodes) to illuminate the markers on the patient P and the LINAC machine L as symbolically represented by the collimator 5. The light from the sources 17B and 18B is reflected as indicated by dashed lines and arrows 17C and 18C extending from the sources 17B and 18B and reflecting back to cameras 17 and 18.

As illustrated a stereotactic immobilizer 42 receives the patient P and may take the form of an evacuated beam bag as commonly used in radiation therapy to immobilize the patient once a correct setup has been established. Alternatively, the immobilizer 42 could be a preformed tray or alpha cradle to define a firm contour of the patient's body for repeat positioning.

Index markers 20, 21, 23 and 24 are fixed on the patient as previously described with reference to FIG. 1. Recall that these markers identify locations marked by radiopaque or MR detectable index markers fixed on the patient P at the time of the CT or MRI scanning. The arrangement in FIG. 2 could be applied on the simulator couch top 11 to simulate a preplan of the treatment setup or could be applied on the couch for radiotherapy as for example a LINAC couch. The radiopaque or MR detectable index markers used during the CT or MR scanner phase can be replaced in the arrangement of FIG. 2 by camera detectable index markers placed at the same locations on the patient. In context of FIG. 2, the camera system C1 determines the 3-D position of the index markers with respect to the camera coordinate system, as discussed above.

In the context of FIG. 2, with the scan data recorded and the position configurations being sensed by the camera system C1, a target P1 within the patient P is established within a treatment volume P2. The target P1 may be the nominal focus of radiation from the collimator 5, and the contour of X-ray dose from the LINAC machine may be intended to engulf the target volume P2. In certain applications, it is desirable to move the target to an isocenter 7 (FIG. 1) for convergence of radiation beams to the target volume P2. Accordingly, as indicated above, the couch 11 may be moved to accomplish the desired coincidence.

Also as noted, the terminal unit 39A incorporates the capability to control and display positional data. Specifically, as indicated, a display panel 39B indicates, in X, Y and Z coordinates, the position of the isocenter relative to a target in real time, e.g. currently, as well as the angles C, G and A (corresponding to LINAC angles 12A for couch rotations, 2A for gantry rotations, and A for collimator rotations as indicated by the arrows in FIG. 1) regarding the beam 6 in the coordinate system of the patient's anatomy in scan data space as rendered from the treatment planning computer embodied in the unit 39.

As described in detail above, the treatment couch 11 carries index markers 30, 31, and 32 which are tracked by the camera system C1 to indicate the instant position of the couch 11 throughout a procedure. As the angles C, G and A are changed during treatment, the position of the planned anatomical targets P1 can be kept at the isocenter 7. In that regard, a feedback controller can be connected from the camera system C1 to the treatment processing system T1 to automatically lock-in the target with the isocenter. For example, the operation could involve an automated and integrated process of frameless optical tracking to accomplish the desired treatment planning parameters and LINAC machine controls for patient positioning.

FIG. 2 also shows alternative types of index markers, for example, marker 50 has a machine recognizable geometric pattern detectable by the camera system C1 to determine the orientation and positioning of the couch top 11. Such markers may take the form of bar-graph patterns, geometric shapes (e.g. triangles), lines, two-dimensional geometric figures and so on, any of which can be detected by the camera system C1 with positions determined by the treatment processing system T1. The detecting and processing of such geometric shapes is well known in the field of optical tracking technology and accordingly it is noteworthy that the discreet index points, as indicated by markers 30, 31 and 32 on the couch top 11 may be replaced by geometric patterns. Also note that index markers 51, 52 and 53 are fixed on the immobilization tray 42. They may be LED's, reflective spherical surfaces, used as augmentational redundancy of the index markers on the patient's body and/or the couch top.

A plate structure 55 illustrates another alternative geometric shape specifically including a triangular plate carrying a plurality of raised spheres 56 along with a linear stripe 57. The plate 55 may be adhered to the patient P indexed by tatoos or other marks. For example, a line 58 may be drawn on the patient P during the CT scan process as a reference. In summary, note that the structure of the plate 55 provides considerable character for indicating the orientation of a patient's body.

Still another form of indicator or marker is exemplified by a strip 60 of reflective tape adhesively secured to the patient P. Again, such a marker can be used as a reference relating to the scan data. Note that by using a comparator algorithm to compare curvilinear geometric objects between the imaging (scan data collection) procedure and the treatment phase (camera space) an indication of the patient's body orientation can be determined and the coordination of target positions managed.

FIGS. 3A, 3B and 3C show other exemplary forms of markers as generally introduced in FIG. 2 that are useable for tracking in accordance with the present invention. FIG. 3A shows a tattoo 61B which may have been made on a patient's skin preparatory for CT scanning. The indicated location would correspond, for example, to the desired placement position for a radiopaque apertured disk or marker detectable during the scanning. Later, preparatory to treatment, a retroreflective apertured disk 61 is applied to the patient precisely as indicated by the tattoo 61B. An aperture or hole 61A is defined in the center of the disk 61 for registration with the tattoo 61B. In an alternative form, the disk 61 may define a reflective dome or spherical surface of a reflective nature for effective camera detection.

In FIG. 3B, a geometric reflective plate 62 of triangular configuration is adhesively secured to the patient P functioning somewhat similar to the plate 55 as considered with reference to FIG. 2. Plate 62 defines holes 63 and 64 to enable precise placement with reference to marked locations on the skin of the patient P.

Another alternative form of marker is shown in FIG. 3C and includes an array of spaced-apart, reflecting spheres 66A, 66B, and 66C fixed to a shaft or stock 65 defining a threaded distal tip 67. In use, the marker is threadable engaged with bone B beneath the skin of the patient P. An example of the marker's use would be to determine the orientation repeatedly of a pelvis location for prostate or gynecological irradiation. Such markers could be percutaneously fixed into the iliac crest bone of the pelvis at one or more locations and remain there for a duration of treatment. The marker also could be put in at the time of image scanning to produce scan data. The array of spheres could then be attached to a stud section emerging from the patient P, for example, at the time of treatment to provide a reflective surface. Clusters or triads of reflecting spheres or other geometric objects or shapes could be attached to one threaded shank adapter to provide both position and orientation information with respect to the pelvis. The spheres could be attached and removed repeatedly from the shank for repeated relocation.

Note generally that retro reflective material as may be used in the various markers as described herein is well known, having a characteristic to reflect illumination substantially back in the received direction. Bright, shiny, or colored surfaces may be alternately used to suit the camera detection needs or discriminate one mark from another. Such surfaces are particularly useful in some applications hereof.

Further with respect to the use of markers as disclosed herein, markers in the form of geometric objects may be attached to indicate positions according to the needs of the various procedures including image scanning, simulator planning and treatment. The patient locations such as the lateral or anterior portions of the skin that are visible to the camera are often advantageous. Orientation of detectable plates, sphere, disks, domes and so on can be determined based on viewing angles of a camera system for optical visibility. Incidently, markers with linear patterns coincident with the alignment of lasers or other fiducials could be advantageous in exemplifying the setup and relocation of a patient on a treatment couch.

Figure 4:
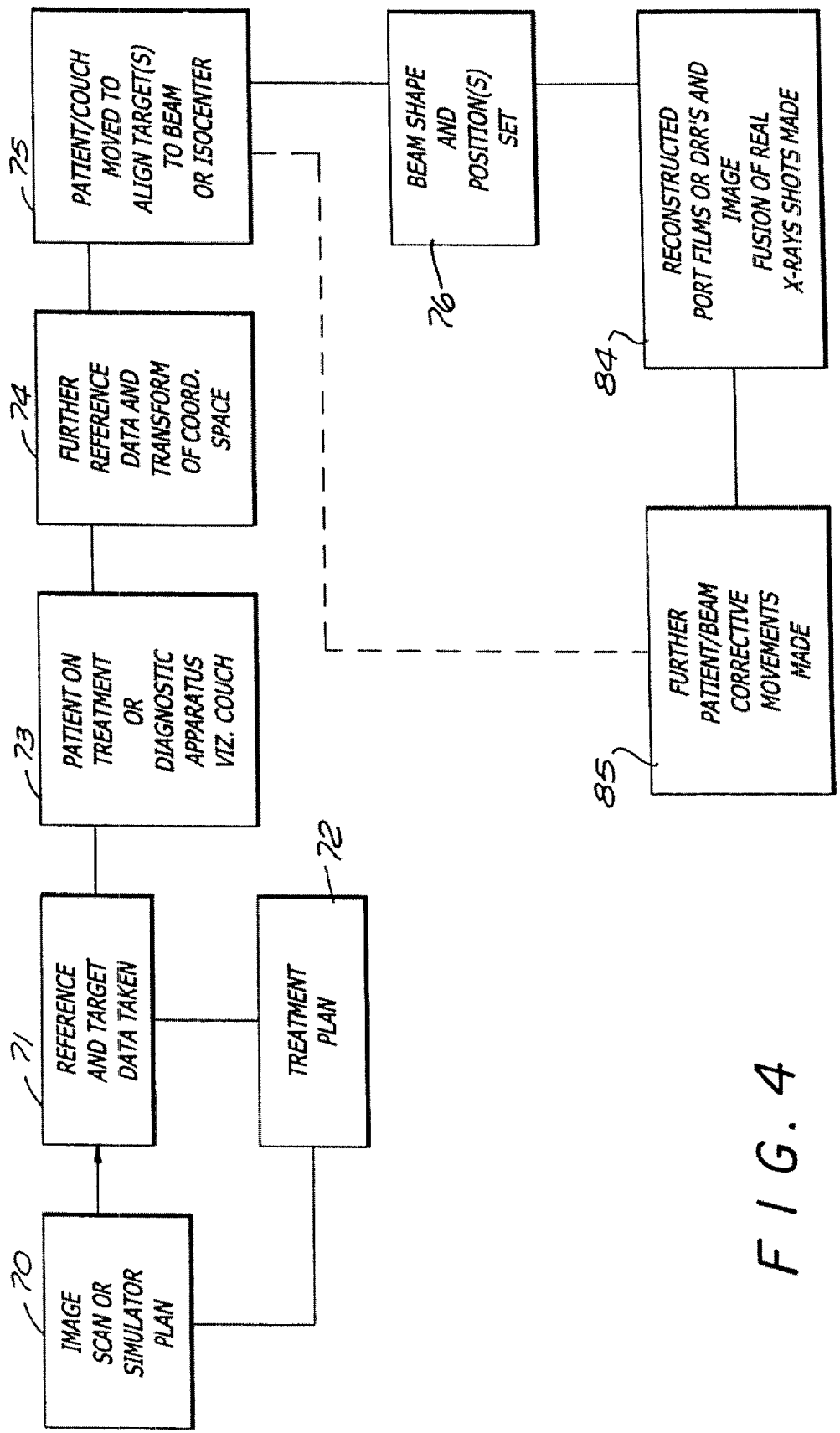
FIG. 4 is a flow diagram describing a process in accordance with the present invention shown in relation to a patient.

Referring now to FIG. 4, consider a process involving the systems of FIGS. 1 and 2. An initial step, illustrated by block 70, is scanning the patient by CT, MR, X-ray ultrasound, PET, or any other modality or by the use of simulators to obtain three dimensional data. A simulator is an X-ray or CT scanning device which has a couch similar to that of FIG. 1, in which X-ray or tomographic image data enables a clinician to establish targets within the body relative to external or internal anatomical landmarks. Image data and information on desired targets are achieved as illustrated by the block 71 (FIG. 3). Such data can be taken with fiducial markers, as described above and in parent cases, to register the data in scanner or stereotactic coordinates. This data is inputted to a treatment planning computer (e.g. system 36, FIG. 1) to establish the treatment plan illustrated by block 72 (FIG. 4). Target position data, along with target volume and beam position data are determined by the clinician in accordance with clinical needs.

After the treatment planning, the patient is put on the couch F with an appropriate setup as illustrated by the step of block 73. Alternatively, during the step of block 73, the patient could be placed on a diagnostic apparatus such as an interoperative CT or MRI scanner. By use of an optical tracking system, as described above, further reference data is taken on the treatment machine, e.g., machine L (FIG. 1) in a step illustrated by block 74 (FIG. 4). Also within the step, a transformation can be made via a computer or comparator (e.g., comparator 37, FIG. 1) to establish the position of treatment plan targets relative to the coordinate space of the camera system.

Next, the distance or difference in position of the planned target from the LINAC (isocenter point 7, FIG. 1) is established and the patient P is moved to align the target or targets with the isocenter of the beam B. The step is illustrated by the block 75 (FIG. 4). Furthermore, the beam positions and shapes of the collimator (collimator 5, FIG. 1) can be established and also set on the LINAC machine L as indicated by block 76 (FIG. 4).

Further refinement of internal target positioning to an isocenter can be achieved by X-ray imaging. As an example of this, referring to FIG. 1, X-ray machine components 80 and 81 are aligned to the axes 14 (horizontal) and 12 (vertical), respectively, and X-ray screen 84 for X-ray machine 80 can thereby determine a digital image of X-rays through the patient's body. A similar screen (not shown) functions with the X-ray machine 81. Further, a portal imager 85 (a common device on modern LINACs) can provide a digital image from the high energy X-rays emitted from collimator 5. Thus, diagnostic X-rays from machines 80 and 81 or high energy X-rays for portal imaging can be used to visualize internal anatomy such as bones and/or radiopaque index markers placed on the skin or implanted in bones or tissue within the patient prior to treatment.

Once the patient position translations described above (based on external landmarks) have been done, then the internal anatomy, which may be more closely represented by, for example, the bony structures within the body, can be further used to verniate and/or qualify the position of a desired internal target to isocenter. For this purpose, the treatment planning computer could provide simulated or reconstructed port film views or digital reconstructed radiograms (DRR's) to simulate such high energy X-ray or diagnostic X-ray images through the patient. These are compared by overlay analysis, image fusion, or other computer theoretic comparative methods to the actual port films or X-ray shots, as illustrated by block 84 of FIG. 4. Based on the comparative images from such reconstructed and actual X-ray views, further incrementation of the X,Y,Z movement of the couch can be made or planned. This is actuated as illustrated by step 85. Again it could be done automatically with a feedback system for fast image fusion comparison of simulated X-ray views.

Another embodiment of the present invention could include a diagnostic apparatus. For example, it may be desired to locate a patient in an CT, MRI, simulator, X-ray, PET, or other imaging machine in an analogous way to the example above of positioning a patient in a LINAC. For an interoperative CT or MRI scanner, it may be needed to move a target from one historic image scan episode to the scan slice plane(s) of the interoperative image scanner to determine the degree of residual tumor during operative resection. Thus the present invention includes use of diagnostic apparatus substituted in the examples given, for example LINACs.

Figure 5:
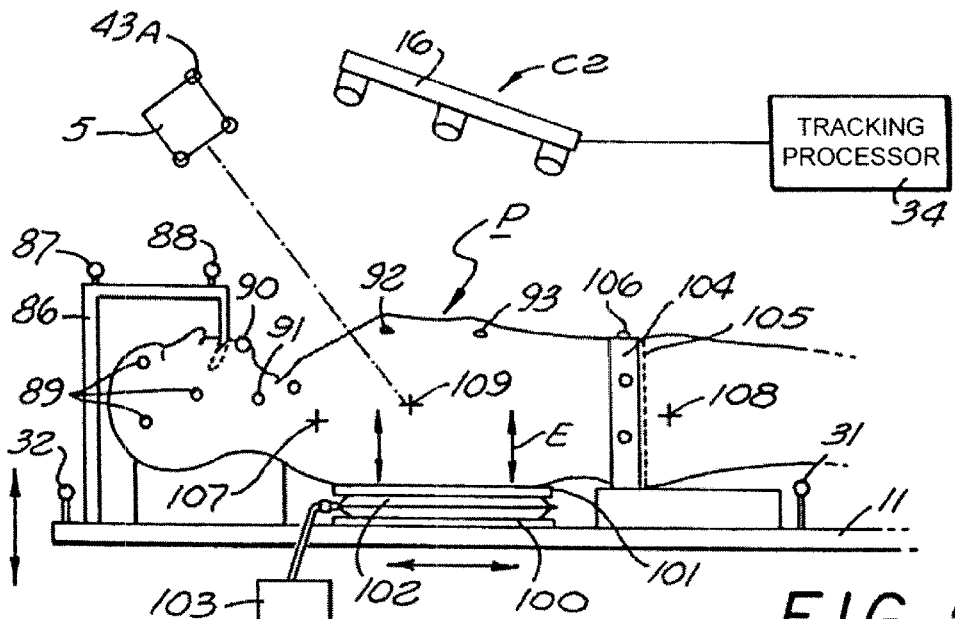
FIG. 5 is a side view showing localization apparatus in accordance with the present invention and shown in relation to a patient.

Referring to FIG. 5, an embodiment of the present invention is illustrated for use in cranial, head and neck, torso, or pelvis application. The cranium of the patient P is stabilized by an arm structure 86 (left) which has attached index markers 87 and 88 for detection by a camera system C2. Various index markers on the patient's head 89, chin 90, throat 91, upper torso 92, and torso 93 are illustratively shown, depending on the clinical application and region to be treated. These indicate the orientation of the patient's anatomy, and enable a comparison of that orientation to the position of the patient during the image scanning phase. As explained above, these index marks could be in the same location as image visible index markers placed on the body during the scanning phase. Alternatively, the index markers could be randomly located or located in position to suit the treatment setup. In that case, the registration from camera space to image scan space can be done by surface fitting, best matching of index points to surface contours, or other similar procedures utilizing index marker positions and surface contours from scan data and camera data.

As shown in FIG. 5, the LINAC or treatment couch 11 has index markers 31, 32, and possibly more not shown. To help orient the torso translations and angulations locally in addition to facilitating possible couch movements, a so-called "tectonic plate" 100 is placed under the patient P. This can be moved in the plane of the couch top 11, as described in a parent application. It can also provide elevation movements which are accomplished by an inflated cushion 102 between an upper plate 101 and a lower plate 100. Inflation of the cushion can be actuated by an inflater 103, which could be manual or electronic. Fine verniations of the height of the torso relative to the head, for example, can thereby be achieved. Monitoring of the position of the torso relative to the head could be done by the camera system C2 by noting the 3D position of such index markers as marker 92 compared to markers on the cranium such as markers 89 and 90.

An alternative means of determining the orientation relative to the LINAC of the pelvis or other portion of the body is achieved by a belt structure 104 which can be placed on the pelvis repeatedly in a similar position. This may be achieved by sticking the belt 104 on or attaching the belt along an index line such as line 105 which is marked by pen on the patient's skin at the time of scanning or simulator planning. The belt 104 may have a multiplicity of physical markers such as marker 106 so that the camera system C2 can determine the orientation of the belt 104 and thus the orientation of the pelvic region relative to the LINAC couch and relative to the isocenter of the LINAC. In this way internal targets such as the target point 107 (in the neck) or a target point in the pelvic region such as at the prostate or cervix 108 could be "driven" or moved to the isocenter position illustrated by point 109 by means of X,Y,Z translations of the couch 11, as described above. Also shown in FIG. 5 is a schematic representation of the collimator 5 with its index tracking markers 43A, etc. so that correlation of beam and bodily positions can be tracked by cameras 16 of the camera system C2.

Figure 6:
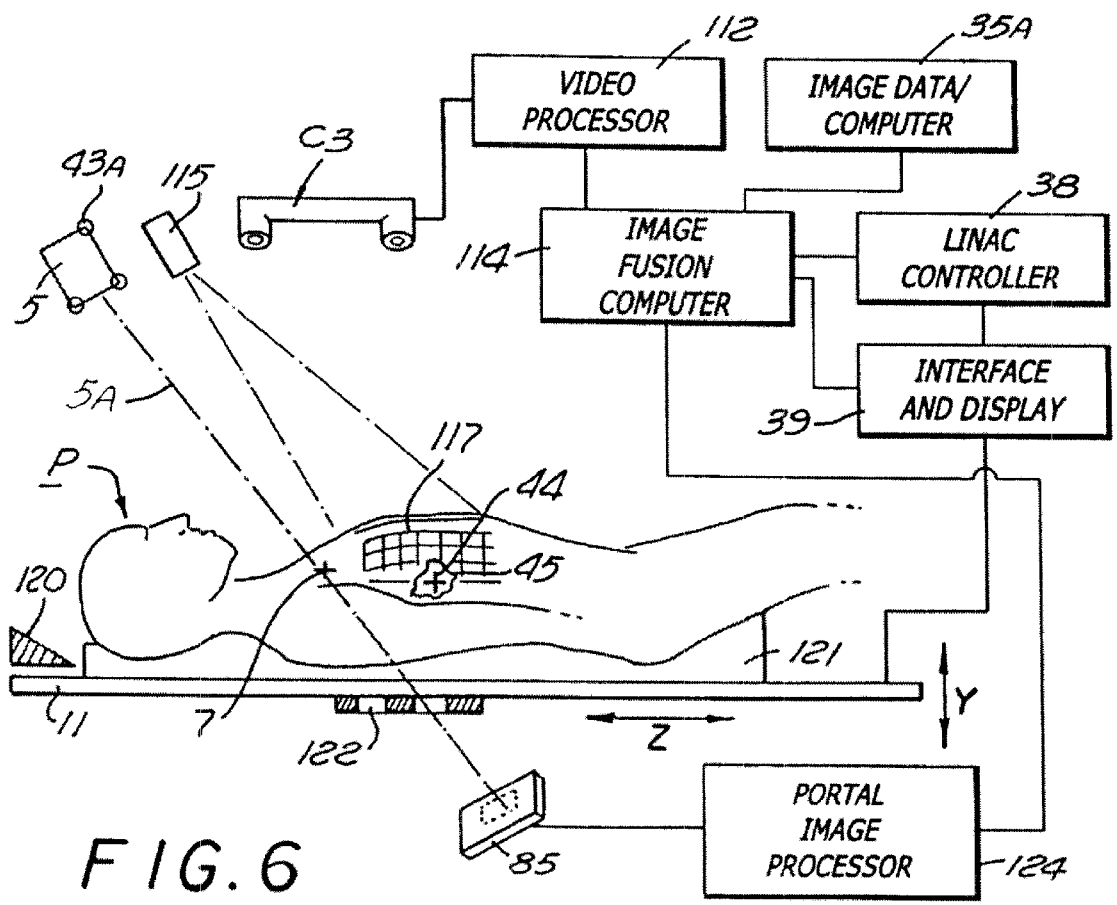
FIG. 6 is a side view of another system for patient localization generally in accordance with the system of FIG. 1.

Referring to FIG. 6, another embodiment of the present invention is shown wherein natural surface contours of the body are fused with reconstructed contours to position the patient P on the LINAC couch top 11. A camera system C3 can be a video camera system to visualize the actual visual scene of the patient P on the couch top 11 and LINAC machine represented by the collimator 5. In this case, the cameras may be unfiltered, two-dimensional CCD cameras which have been calibrated for stereoscopic viewing. Two, three, or more cameras can be used. Some can be filtered for infrared reflective viewing and others could be unfiltered for direct video imaging. They can be mounted on the ceiling of the LINAC room (fixation not shown). Alternatively, the cameras of the system C3 could be individual and separated, each located for example on the walls or ceiling of the LINAC room.

An illumination system 115 also is represented which projects a grid of light onto the patient P, illustrated by lines of a surface 117. This could be a pattern of structured light with areas of light and dark and linear light arrays in two dimensions projected onto the patient's body surface. Such a light array can be recognized and registered by pattern recognition algorithms in a video scene. The VISLAN system developed by A. Colchester illustrates methods of such surface reconstruction, as disclosed in an article "Development and Preliminary Evaluation of VISLAN, A Surgical Planning and Guidance System Array With Operative Video Imaging"; A. C. F. Colchester, et al., Medical Image Analysis, Vol. 1, pp 1–18, Oxford University Press, 1996.

Information from camera system C3 is represented by signals applied to a video processor 112 to capture the video field of view and to reduce the locus of points of structured light on the surface 117 to a set of three-dimensional points in space relative to camera coordinate. Thus a rendering of a portion of the surface of the patient's body can thereby be done. The cast light could be by laser or pattern projection and could be in different frequency ranges (visible or infrared) as different colors and patterns to better differentiate patterns and backgrounds.

Image scan data, supplied by a data computer represented by a block 35A, also can be segmented to render the reconstructed surface of the skin of the patient P. See by reference the XKnife System of Radionics, Inc., Burlington, Mass. This would provide an analogous computer graphic rendering of the same surface information as in the video processor 112. Those two surface data sets can be input to an image fusion computer 114 which implements an image fusion algorithm to fuse the video surface and the reconstructed image base surfaces described above. This can be done by a chamfer algorithm, an example of which is embodied in the Image Fusion algorithm of Radionics, Inc., Burlington, Mass. Such an image fusion of surfaces provides a registration of the 3D data set from the image scan to the coordinate system of the video processor. This is a transformation from the stereotactic image data set of the image scanner to the 3D coordinate system of the camera system C3. Since the camera is also registered relative to the external LINAC apparatus, its couch, gantry, and collimator, this provides a transformation of the image data set to the coordinate space of the LINAC.

As illustrated in FIG. 6, in the process of treatment planning, a target point 44 and target volume 45 are determined in the body and rendered in the image scan data of the data computer 35A. The coordinates of these structures in turn are transformed as just described to the coordinate system of the camera space. Therefore, the position of the target point 44 in the camera space is "known" by the camera system and its associated optical processing and computer storage processor 112.

The output from the video processor 112 and the image data plus treatment planning data from the data computer 35A enter the image fusion computer 114. After image fusion of the reconstructed image data surface and the video detected surface, the target coordinates and target volume information from the computer 114 are sent to the LINAC controller controls 38. This will enable either manual positioning of the anatomical target 44 to the LINAC isocenter point 7 or actuate automatic controls to do the same. The user interface and display system 39 enables the clinician to assimilate all of this information visually and to actuate the movement of the couch 11 for the translation just described. These movements are indicated by two of the coordinates, Y and Z in FIG. 6.

Also shown on the couch 11 are various geometrically detectable index structures 120 and 122, which can be detected by the video camera system C3 and their position determined in 3D space. This will monitor and control the position of the couch 11 and control the movement of the couch during corrective changes. An immobilization cushion 121 is also shown which can help in certain clinical situations to prevent movement of the patient.

Also shown in FIG. 6 is a portal imaging system 85. Such portal-imaging digitized detectors are common on commercially available LINACs today. A beam from collimator 5 (representing the LINAC) is sent generally in the direction of the principal axis 5A, through the patient's anatomy and passing by isocenter point 7. Bony structures within the patient's anatomy will be seen on the digital portal image. Once the patient's body has been moved to the desired position by the video tracking described above, such a portal image can be taken at particular gantry, couch, and beam positions. From the 3D image data, a reconstructed projected portal image to render the skeletal details inside the body can also be generated to simulate the same direction of the beam in physical space. A correlation or difference in positioning of the portal image compared to the reconstructed portal image will also give information on translation and rotation corrections for the patient positioning on the couch 11 with respect to the LINAC machine (collimator 5) so as to bring these two portal image views into closer registration. This can give incremental values of X,Y, and Z to further verniate the desired target spot to the isocenter. By reference, note the article entitled "Automatic On-Line Inspection of Patient Set-Up in Radiation Therapy Using Digital Portal Images," by Gulhuijs, K. G. A. and vanHerk, M., Med. Phys., 20(3), May/June 1993.

Also shown in FIG. 6 is the portal imaging processing electronics and computer indicated as a block 124. This processor develops data from the portal image detector 85 to render two-dimensional projected views through the patient's anatomy. This data, with image information, is then supplied to the image fusion computer 114 to enable image correlation with respect to reconstructed portal images from the image data computer 35. Image fusion computation in the computer 114 thereby derives LINAC control parameters which are sent on to block 38 to actuate patient verniated movement.

Figure 7:
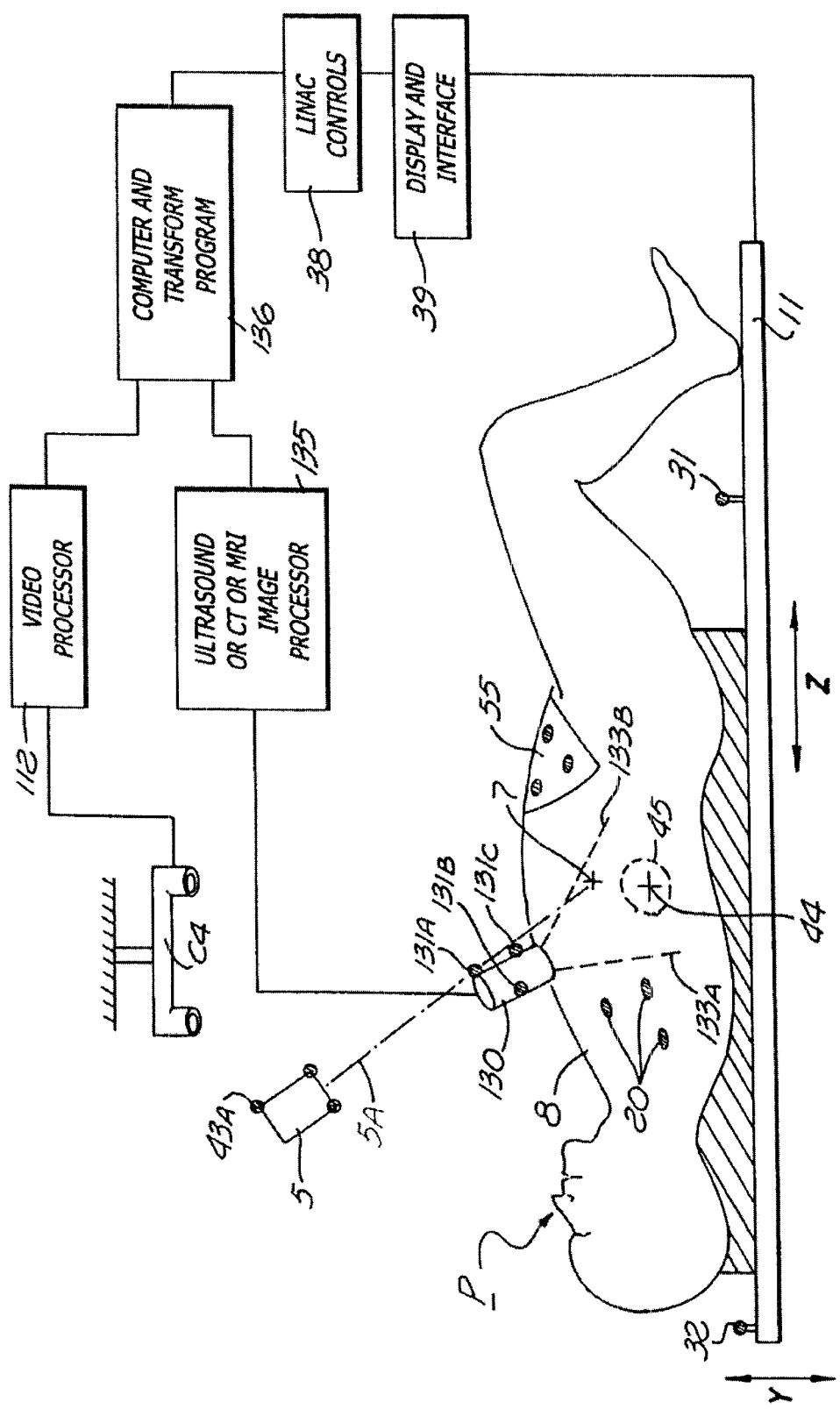
FIG. 7 is a side view of an optical and ultrasound positioning system on a treatment machine in accordance with the present invention shown in relation to a patient.

Referring to FIG. 7, another embodiment in accordance with the present invention is shown to provide target and patient positioning. An ultrasonic detector 130 (center) creates ultrasonic image data within an image field indicated by dashed lines 133A and 133B. Within that field an image of internal anatomy is detected and processed by an associated ultrasonic processor 135. This can include a display of the actual image. Such ultrasonic images are commonly used clinically, for example in equipment made by Aloka Corporation of Wallingford, Conn.

Index markers 131A, 131B, and 131C are attached to the ultrasonic scanner 130 so that camera system C4 can detect in three dimensions the orientation of the ultrasonic unit relative to the patient P. Other index markers may be placed on the patient's body such as marker 20 for purposes of registration of the body anatomy as well. Thereby a target point 44 can be identified, and because its position is known in the coordinate space of the ultrasonic imager 130, and because the position of the ultrasonic imager 130 is known in the coordinate space of the camera C4, then the position of target point 44 can be known by appropriate transformation in the coordinate space of the camera C4.

A target volume 45 also can be detected by the ultrasonic detector 130. Its 3D position may also be thereby determined in the 3D coordinate space of the camera system C4. This, then, illustrates an example of a real-time image scanner to provide updated positioning of internal organs and tumors. Use in soft tissues such as prostate, breast, head and neck, larynx, liver, and so on can enable corrections to organ shift that may occur from initial CT, MR, or other scanning. Computer 136 can compare or image fuse current ultrasound images from the processor 135 to historic scan data and/or camera position data to make body position corrections. Position corrections and interface display by LINAC controls 38 and display 39 are similar to the examples given previously to move target 44 to isocenter 7 of beam 5A of LINAC collimator 5. A similar example to this could substitute an interoperative CT or MR scanner for the ultrasonic image, with optical index markers analogously attached to the CT or MR interoperative scanner.

Figure 8:
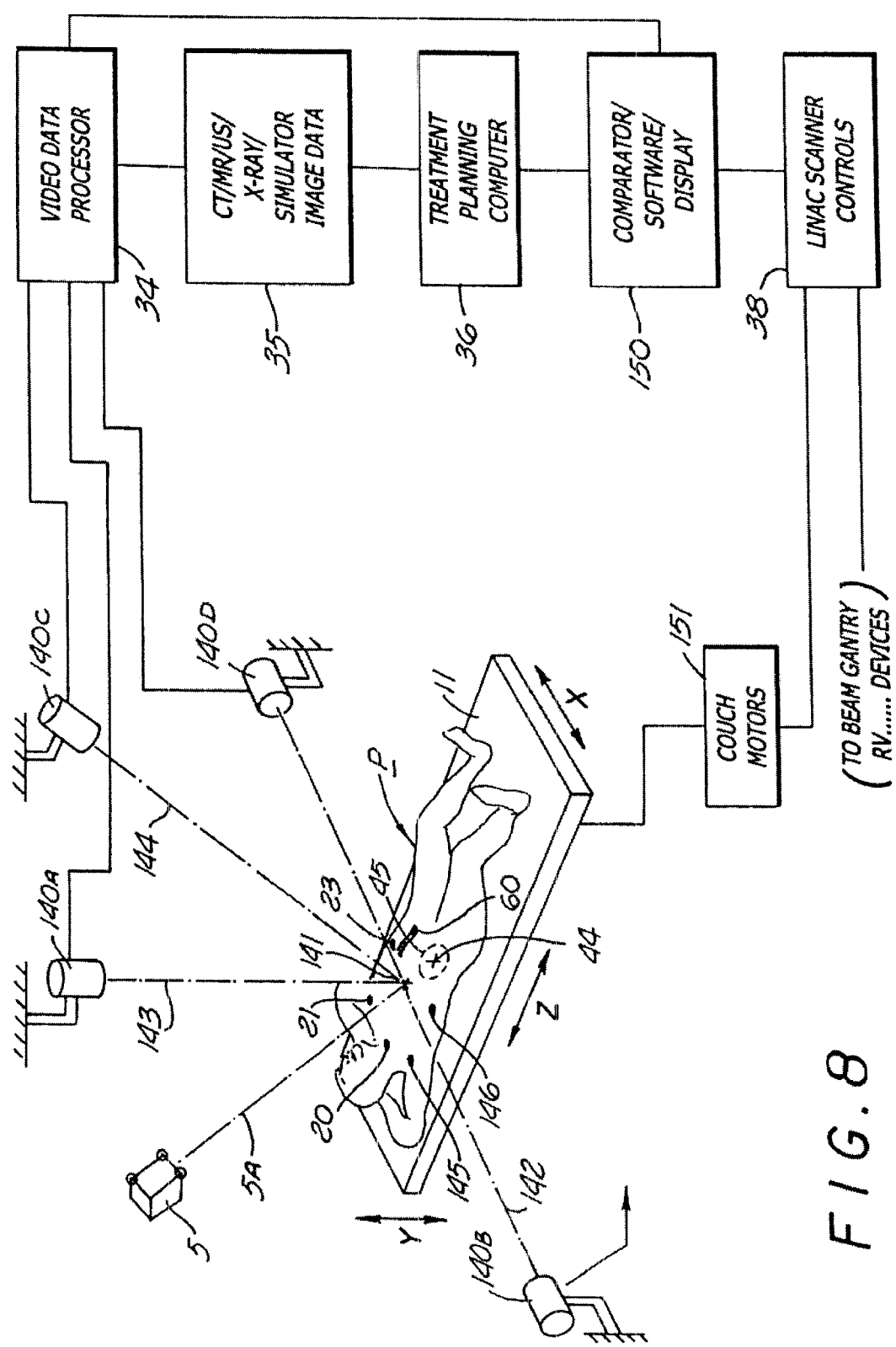
FIG. 8 is a perspective and diagrammatic view showing a video positioning system in accordance with the present invention shown in relation to a patient.

Referring to FIG. 8, another embodiment in accordance with the present invention illustrates the use of multiple video cameras to reposition the body on a radiation treatment or simulator couch. Cameras 140A, 140B, 140C, and 140D view the patient's body from a variety of orientations. More or less numbers of video cameras could be present in this embodiment. In a particular arrangement, cameras 140B and 140D are colinear and opposed, viewing along a central axis 142. Camera 140A views along a separate principal axis 143, which may be orthogonal to the axis 142. Camera 140C may be viewing from an oblique axis 144. Axes 142, 143, and 144 may be prealigned to intersect at a point 141. For example, the point 141 may be precalibrated to be the LINAC isocenter.

The collimator 5 has a central axis 5A (beam) which also may pass through the point 141 as the isocenter of the radiation beam as well as the camera views. It is not necessary at all the camera axes have coincident axes. They may be set at arbitrary directions and calibrated to the scanner or treatment machine coordinate space in a manner described in connection with FIG. 10 as described below. By precalibration, the position of the isocenter 141 may be known virtually in the camera coordinate space of each of the cameras and in each of the camera views. This may be convenient, depending on clinical setting and patient and treatment setup. One of the cameras also may be tracking the position of the couch 11 and another camera may track the collimator 5 geometry and specifications of the LINAC space and room. The cameras may have a known calibration in the 3D space of the room. An example of a calibration procedure and system is shown below.

Also shown in FIG. 8 are index mark positions 20, 21, 23, 145, 146, and index line 60. Similar to the description above, these may be radiopaque or MR visible markers which can be "seen" in the image scan data. Their position may be referenced on the body by ink marks, tattoos, or lines which are visible by video cameras 140A, 140B, 140C, and 140D. Index markers 20, 21, and 23 may be discrete or geometric objects similar to those described above placed at positions on the upper or anterior surface of the body. Markers 145 and 146 may be multiple markers on the lateral portion of the body. Similarly, geometric objects such as stripes, triangles, or recognizable patterns of lines or shapes, illustrated here by the example of linear objects 60, could be similarly placed so that they are visible to one or more of the cameras at the same time. These can be used as described below to provide reference points to correlate real video images of the body to reconstructed video representations or simulations of the body based on image scan data.

The electronic signal output from the cameras 140A, 140B, 140C, and 140D may be processed by video electronics, indicated by the processor of block 34 in FIG. 8. The processor 34 provides power and strobe signals to the video cameras. Output data from the video cameras generates electronic signals for a display unit 150 which includes a comparator, display software and a display device, such as a CRT. Real video views of the patient's body on the treatment couch top 11 can be reduced to digital displays in a calibrated relationship in terms of their magnification, relationship to the isocenter point 141, and relationship to other points in the 3D space of the treatment/diagnostic room.

The block 35 in FIG. 8 provides the image scan data taken from CT, MR, ultrasound, X-ray, PET, simulator, or other modalities. This data is input into a planning computer 36 and used to determine targets, beams, etc., as described above. The external anatomy of the patient's body, i.e. the skin, can be-rendered as a 3D surface in the space of the image data by the computer 36 (see for example the XKnife planning system of Radionics, Inc., Burlington, Mass.). The image scan data can also include both locations of the mark points 20, 21, 23, 145, 146, or mark objects such as 60 by use of appropriate scan-visible scanner index markers placed at these positions during image scanning. Also, projected views or simulated reconstructed views of such 3D surface renderings can be developed by planning computer 36 to simulate video views from any direction. Similarly, projected positions of the scanner index markers onto the 2D reconstructed views for each video camera can be developed in computer 36. Such reconstructed video views in the directions of axes 142, 143, and 144 are created by computer 36 based on the image scan data in image scan coordinates.

Selected target point(s) such as 44 or a target volume 45 are contoured and segmented by the clinician in computer 36. The projected 2D reconstructed video views, including projected target positions for target 44 and volume 45 from the 3D image data can be input into a comparator system 150, which may be the same computer 36 or a separate computer with graphic display means. Thus, in the comparator computer 150 input data from the real video views and data from reconstructed video views can be compared, merged, image fused, or rendered contemporaneously. In this way, the position of the target point 44 or volume 45 from the image scan space may be seen relative to the coordinate space of the camera views. Also, the projected view of isocenter 141 can be displayed in each video view so that the operator can determine the couch or patient translation(s) within each of the views to bring the selected target point 44 into coincidence with isocenter point 141. Such translations can be represented as output from the comparator system 150 to, for example, the LINAC or diagnostic control system 38. The LINAC/scanner controls can provide signals to the couch motor system 151 to enable X, Y, and Z translation of the couch so as to move target 44 into physical coincidence with X-ray beam or imager isocenter 141. When so done, the X-ray beams from collimator 5 will converge on the isocenter and therefore the target point. For a LINAC, dosimetry from the planning computer 36 may be delivered by means of the appropriate orientation and collimator shape out of the LINAC collimator 5. Control of the couch position, gantry movement, beam configuration (for example a multileaf collimator or shaped beam collimator), as well as data to record and verify system can be output from the LINAC control system 38. The process of patient positioning, monitoring, position feedback, dose delivery, and angulation of the beams can be carried out manually or by automatic control.

Figure 9C:
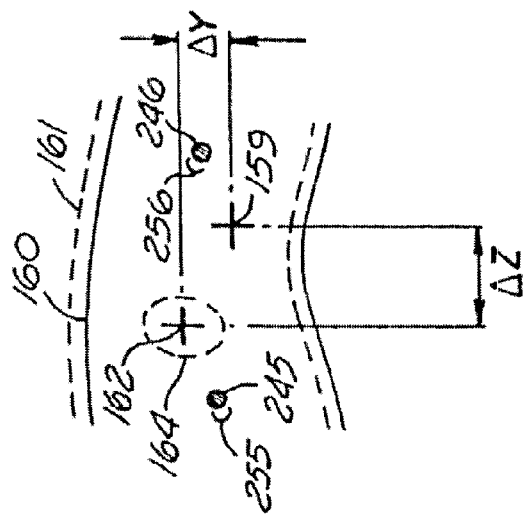
FIG. 9 is a series of views 9A, 9B and 9C illustrating video and graphic reconstruction fusion in accordance with the present invention, shown in relation to a patient.
Figure 9B:
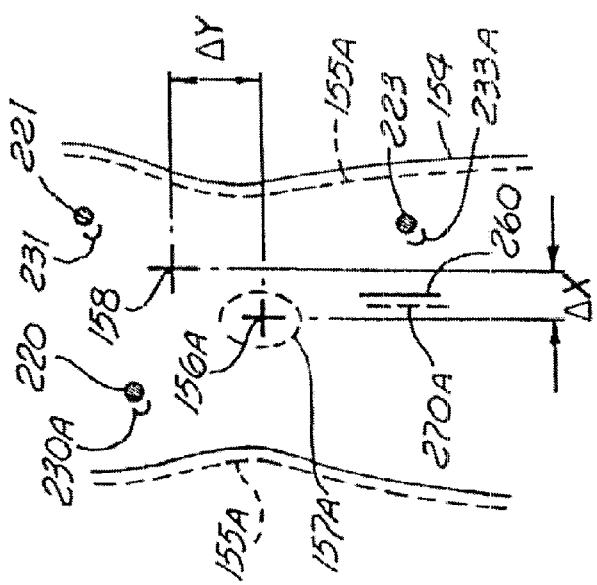
Figure 9A:
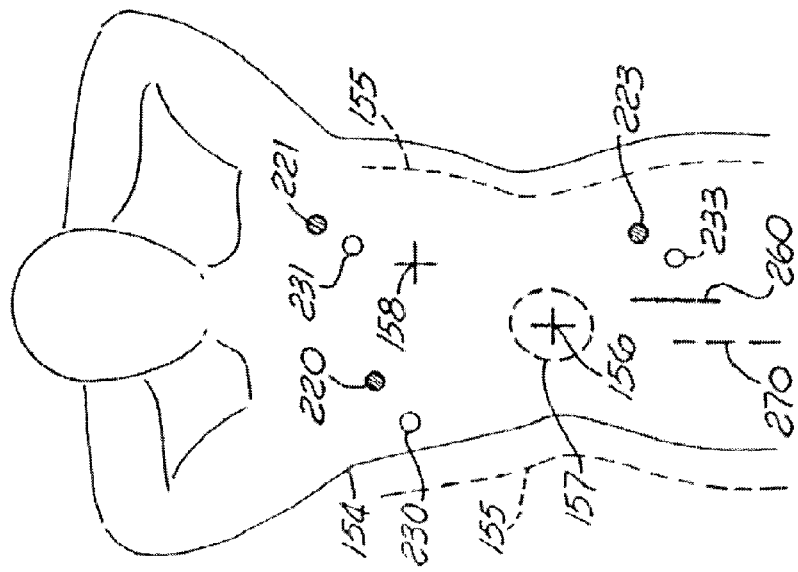

Referring to FIG. 9, exemplary images are shown that may be rendered from the comparator computer and software and display means 150. These may be views on a computer graphics screen, CRT, liquid crystal display, or other display means or alternatively graphically output by printout. In FIG. 9A, the solid line 154 represents the projected outline of the patient's torso as viewed, for example, by camera 140A in FIG. 8. It may represent the direct video image of the patient's body on couch 11. It may be enhanced by appropriate illumination, structured light scanning, laser beam wash over the surface, infrared lighting, or just natural lighting. Point 158 may represent the position of the beam isocenter 141 as projected into the view plane of camera 140A. The cameras may be precalibrated prior to the setup so that the projected position of isocenter point 158 can be calibrated within this field of view of the camera 140A.

The dashed line 155 represents the boundary of the external contour of the body from the projected reconstructed view derived from the prior image scan data along an axis parallel to axis 143. Dashed lines 155 then represent a computer generated contour of the external projection of the patient's body to simulate the actual video boundary line 154. The non-coincidence of dashed line 155 compared to solid line 154 in FIG. 9A represents the degree of translational shift or body movement needed to bring the lines into registration. Projected target position 156 and volume outline 157 are shown in the reconstructed video views based on imaging data.

Also shown in FIG. 9A are the positions 220, 221, 223, and 260 of discrete geometric optical index markers detectable by camera 140A that are located in the positions corresponding to markers 20, 21, 23, and 60 in FIG. 8. These can be the position of discrete geometric scanner index markers placed on the body during the scanning phase and image data collection. In the reconstructed view of the image scan data according to the direction of camera 140A, positions of objects 230, 231, 233, and 270 correspond to the reconstructed projected views of the scanner index markers, as seen in the image data. For correct alignment of the reconstructed image scan projections to the actual video projections, the markers 230, 231, 233, and 270 should coincide in the camera coordinate space to camera marker coordinates corresponding to the optical index markers 220, 221, 223, and 260.

FIG. 9B illustrates the result of a computational translation of the dashed line 155 to coincide with the solid line 154 from FIG. 9A. In FIG. 9B, the dashed line 155A (which is the translated and/or rotated analog of external contour line 154 in FIG. 9A) is now lying close to the solid video image outline of the external surface 154. Bringing the two lines 154A and 155A into coincidence can be done manually by the operator by manipulation of the display in 150 or it can be done automatically by a mathematical algorithm in 150 which recognizes the two lines and image fuses them by a line minimization approximation, chamfer algorithm, or curve fitting process. This would give rise, therefore, to a virtual positioning of the selected target point 156A and volume outline 157A with respect to the actual video projection line 154. With this registration having been done, then the associated translation shifts ΔX and ΔY, as shown in FIG. 9B, can be determined from the display or the computer output of 150. Thus ΔX and ΔY correspond to the translations of the couch 11 in FIG. 8 required to bring the selected target point 156A into coincidence with the isocenter point 158 as viewed in the projection parallel to axis 143. In this example, the patient is lying substantially horizontal on the couch top 11 in a similar position to the orientation of the patient on a CT couch, for example, where a horizontal is established. Otherwise, a sequence of rotations and translations can be implemented mathematically for a similar coincidence of target point to isocenter point for multiple camera views.

In the situation that non-natural scanner index markers are used, such as elements 20, 21, 23, and 60 in FIG. 8, it may be convenient to use the camera marker coordinates in the 2D projected views for these elements, as shown in FIG. 9A, to produce the translation and/or rotation of the patient's body so that the video image and the reconstructed video image (from the image data) coincide. Shown in FIG. 9B is the resultant coincidence of reconstructed scanner marker coordinates as projected into the video camera views with the camera marker coordinates from the optical index markers detected by the cameras themselves. Here the translation and/or rotation of the body is such that the camera marker coordinates 220, 221, 223, and 260 coincide with the reconstructed positions of the scanner index markers 230A, 231A, 233A, and 270A. Use of such geometric objects could have certain advantages when illumination levels and circumstances make difficult the visualization of the external borders of the patient's anatomy for the image fusion to the reconstructed external borders, as described above. Either one or the other method may be used and advantageous according to a given clinical situation.

Referring to FIG. 9C, a projected view of video surface contour 160 as seen from video camera 140B is brought into coincidence with a reconstructed video view from direction 142 as determined in treatment planning computer 36. The external contour of the patient's body is indicated by the dashed line 161. The appropriate mathematical shifting of the treatment planning external contour has been done in 150 so as to bring these projected surface contours into coincidence, as discussed in connection with FIGS. 9A and 9B. Furthermore, the target position 162 and treatment volume 164 can be rendered in the projected 2D view of the 3D data from the image scanning, and these also are shown in FIG. 9C in relation to the real video contour 160. The component distances ΔY and ΔZ similarly correspond to the couch translations to make the target point 162 coincide with projected isocenter point 159.

As an alternative, or in addition, also shown in FIG. 9C are the optical index markers 245 and 246 corresponding to scanner index markers placed on the locations 145 and 146 shown in FIG. 8. The scanner marker coordinates for these scanner index markers can be developed in the image scan data, as described above, and rendered from the data processing or treatment planning computer as reconstructed scanner marker coordinates or sets of coordinates, as illustrated by the circles 255 and 256, shown in coincidence in FIG. 9C with the optical index marker positions 245 and 246. It can be that for the various views of cameras 140A, 140B, 140C, and 140D of the example in FIG. 8, that location of such optical index markers corresponding to scanner index marker positions can be placed conveniently on the frontal, lateral, or oblique surfaces of a patient's anatomy for this purpose.

It is noted that in some circumstances such scanner index markers and optical index marker positions may be convenient for real-time video repositioning of a patient's body, as illustrated in the example of FIG. 8 and FIG. 9. This may be an alternative to or an augmentation of a purely external contour or 2D surface contour projection or a 3D surface contour matching of natural anatomical landmarks.

The example of FIGS. 8 and 9 illustrates an apparatus and method which is in accordance with the present invention that does not require predetermined fiducial markers to be placed on the external anatomy or use of structured light illumination. In the situation where no scanner index markers are used, the system and method of the present invention can rely on natural landmarks such as surface contours or edges of external body surfaces to be brought into registration in a virtual view of image data compared to an actual video view of the real scene. The increase in the number of cameras from many view angles such as camera 140C at an oblique viewing angle 144 increases the input data on the real external surface. The corresponding matching or surface fusion of the reconstructed surface from image scan data to data on the surface from multiple camera views will improve with the increase in camera number and views. The number of cameras and the degree of such registration may depend on the clinical circumstances and the particular body region that is being treated. Such registration could have application in the cranial, head and neck, torso, abdominal, and pelvic, or even limb extremity for treatment using external beam irradiation or for diagnostics using a CT, MRI, or other scanner type. In this connection, reference is made to use of video cameras in a treatment planning room in the paper by B. D. Milliken, et al., entitled "Performance of a Video-Image-Subtraction Based Patient Positioner System," Int. J. Radiation oncology Biol. Phys., Vol. 38, pp. 855–866, 1997.

Figure 10:
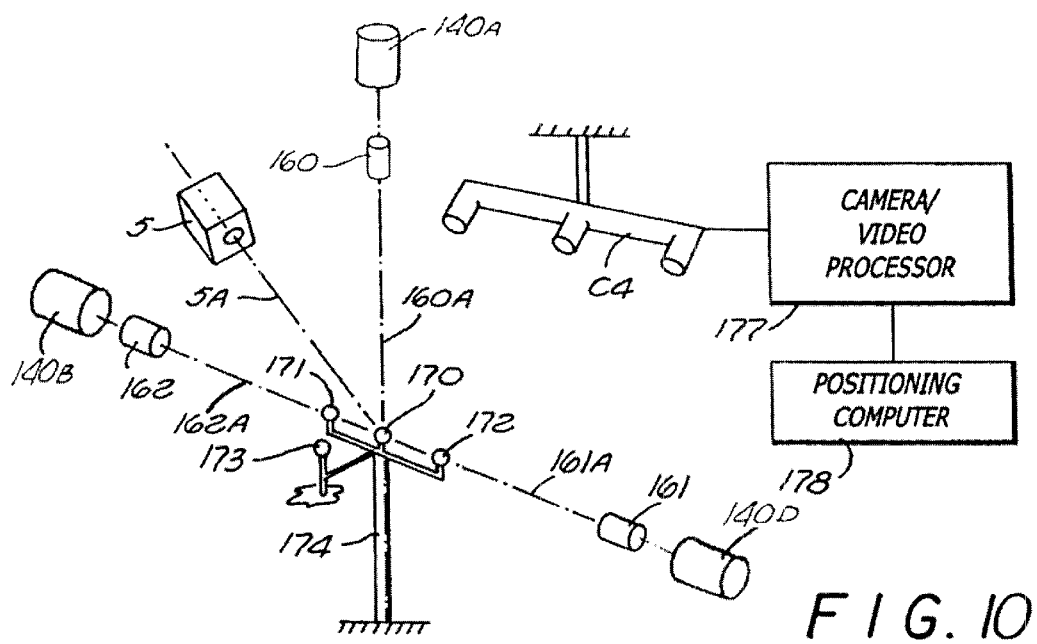
FIG. 10 is a perspective and diagrammatic view showing an apparatus for calibrating or aligning optical cameras with respect to a treatment machine in accordance with the present invention.

Referring to FIG. 10, apparatus is shown for calibrating a camera system to the isocenter position and principal axes of a treatment planning machine, image scanner, or simulator. Camera system C4 is positioned to view the treatment or imaging field. The lasers 160, 161, and 162 are positioned to send laser beams 160A, 161A, 162A to converge at a common point. This point, for example, may be the isocenter of a LINAC. Alternatively, the lasers could cast sheets of light in planes which include the isocenter. At the isocenter is placed a marker object 170, which may be a source of light, a globe-emitting light, an LED light source, a retroreflecting sphere, a reflecting geometric object, an object with a specific geometric pattern of lines, crosses, diamonds, other objects, and so on which would indicate the position of the intersection of the laser beams and therefore the position of isocenter. Camera system C4 detects the field including the object 170. Since this can be registered in the output data from the video cameras, which is processed by a CCD camera or video camera processing electronics and computer 177, then the electronic data corresponding to the 3D position of the object 170 is thereby determined. The camera processor 177 can store that position, and when 170 is taken away and a patient put in place, then 177 can refer to all other 3D points in space with reference to it. In this way, camera system C4 is calibrated with respect to its 3D coordinate space and in respect to the point corresponding to isocenter where the object 170 is placed. The object 170 could be pre-aligned and calibrated with the laser beams 160A, 161A, 162A by a series of light detection measurements prior to camera calibration. (By reference, see the MIS Mechanical Isocenter Standard of the XKnife System by Radionics, Inc., Burlington, Mass.).

Also shown in FIG. 10 are video cameras 140A, 140B, and 140D, which are analogous to those used in the embodiment of FIG. 8 in accordance with the present invention. These could be an alternative or an augmentation of the camera system C4 according to the clinical needs. The cameras 140A, 140B, and 140D are shown in this example colinear with the lasers 160, 162, and 161 only for the purpose of illustration. Indeed, the video cameras and the lasers may be very close together or the laser beams may be delivered colinearly with the cameras by means of split prisms or beam-splitting mirrors so that the lasers themselves do not obstruct the camera view. The calibration structure 174 may have additional markers visible on lateral views such as 172, 173, and 175 to give a perspective and magnification calibration for the lateral cameras 140B and 140D. The video cameras 140A, 140B, and 140D may be used for repositioning external contours of the patient or may be used to develop video data of optical index markers to produce camera marker coordinates in accordance with the discussion above. With three or more non-colinear points in any camera projection, perspective use of the cameras can be developed whereby calibration of the cameras relative to, for example, the isocenter of a linear accelerator could be made and embedded in the positioning computer 178 in FIG. 10.

Also, to calibrate the laser axes in the coordinate space of the cameras, other objects such as 171, 172, and 173 are placed in known positions relative to these axes, and also detected by camera system C4. Again the camera processor 177 can record this data and determine in its stereoscopic 3D coordinate frame the position of the axis points 171, 172, and 173 as well as the origin point 170. In this way, the 3D coordinate system associated with imaging scanning, simulator, or treatment machine can be calibrated and transformed into the 3D coordinate system of the camera system C4.

A processing computer 178 may also be connected to the camera processor 177 for the purpose of storing such spatial information and for the purposes of registering other 3D points which may come into the field of view of the cameras relative to the transformed coordinate system as described above. When a patient is placed on a LINAC treatment table with a calibrated camera system C4 and with appropriate registration or index markers on the patient and the LINAC apparatus, then all of the physical objects such as the patient's body, the treatment couch, and the LINAC collimator 5 can be detected and can be mapped into the coordinate system defined by the isocenter and the laser axes. The use of orthogonal lasers to define isocenter is commonly used in modern day LINAC treatment setups.

Figure 11:
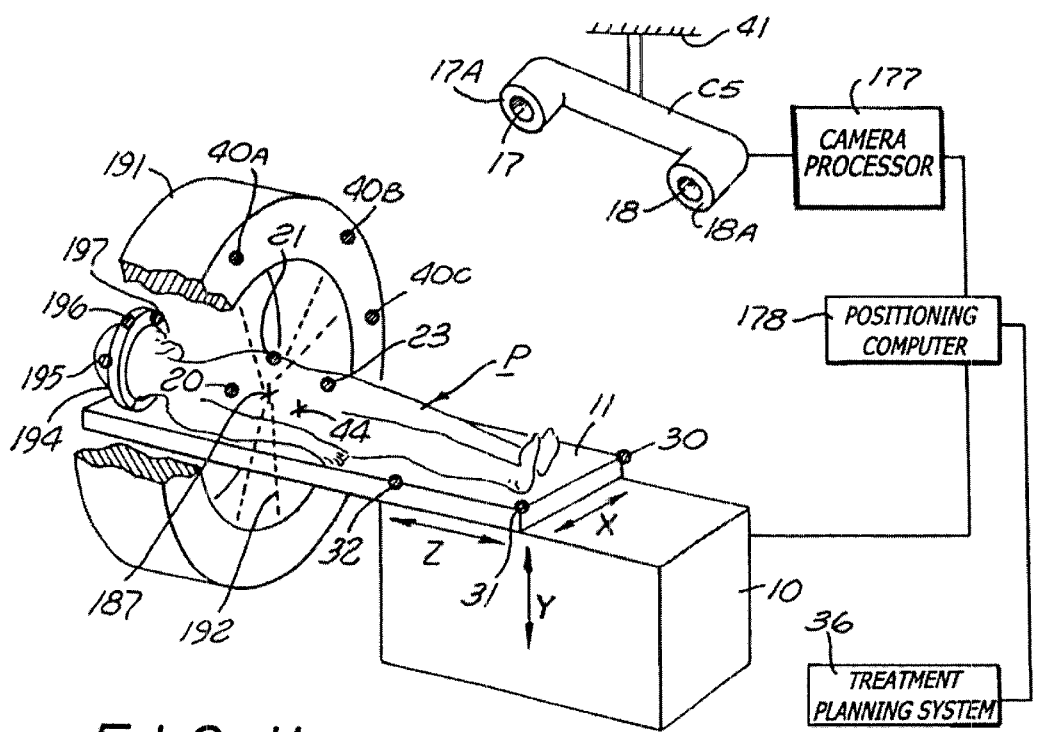
FIG. 11 is a perspective view showing another embodiment of the present invention involving frameless stereotactic navigation on an image scanning machine apparatus and shown in relation to a patient.

FIG. 11 illustrates another embodiment in accordance with the present invention wherein the use of camera tracking of the patient and apparatus is associated with an image scanning apparatus as described previously. As in the above description in connection with previous figures, the patient P is on a couch top 11. The couch top 11 may have X, Y, or Z movement, or, in the case of some CT scanners only, movement in the vertical and longitudinal directions, Y and Z. The couch top 11 has optical index markers, patterns, geometric objects, or other identifiable structures indicated by 30, 31, and 32. The associated apparatus 191 is shown as a toroidal scanner as for example for a CT, MRI, or PET scanner. This could be a C-shaped MRI magnet or other configuration of image scan device. Typically, X-ray fields or electromagnetic fields emanating from apparatus 191 for CT or MRI scanning are used to perform volumetric or tomographic scanning on the patient. These fields are schematically illustrated by the dashed line such as 192. In accordance with the previous description, optical index markers or fiducial points, illustrated for example by objects 20, 21, and 23, are placed on or in proximity to the patient's skin. As described above, these could be natural landmarks, or they could be other geometric objects such as spheres, discs, pattern plates, etc. They are visible when the patient is in certain positions to the field of view of camera system C5. In FIG. 11, only a two camera system C5 is shown which includes cameras 17 and 18. There is an annular, light-emitting ring 17A and 17B around the cameras in the case that reflective optical index markers are used on the patient or the apparatus. On the CT, MR, PET, or apparatus 191 are index markers 40A, 40B, and 40C, and there may be more according to the need. These are "visible" also to camera system C5. Thereby the location of the imaging apparatus relative to the patient can be determined in the 3D stereoscopic coordinate space of camera system C5. The video or camera processor 177 is integrated with comparator system and couch controller 178 and/or coupled to a treatment planning system 36 in accord with the description above. From prior image scan data, a target 44 may have been identified in the patient's body. It may be desired, according to the clinical need, that rescanning for example in the operating room or in the treatment room is needed to assess the tissue volume near the historically determined target 44. The image scan machine may have a reference point indicated in FIG. 11 by the point 187. This could be, for example, the nominal convergence point of X-rays in a CT scanner or some calibrated geometric point in the space of an MRI scanner reconstruction volume. Alternatively, it could simply be an arbitrary point which is determined by a calibration process within the coordinate space of or on the image scanner. A relationship of this reference point 187 to the external apparatus 191 and its associated optical index points 40A, 40B, and 40C can be precalibrated or determined, and therefore the camera system 16 may have in its memory storage, or in direct view, a determination of where the reference point 187 is relative to the other objects such as the patient's body and its associated index marks 20, 21, and 23.

As one illustrated example, a patient may have been scanned by CT or MR to determine the position of a tumor in his body or his cranium. Based on that information and a treatment planning processor such as 36, surgery or other intervention may be planned. It may be desired to determine the degree, for example, of the tumor as the resection is taking place. In this situation, a CT, MR, PET, or other scanner may be placed in or near the operating room, and during the surgery a scan of the patient is required in or around the region where the tumor was identified by the previous imaging, and/or around the region where the surgeon is resecting. In that case, use of the optical tracking system as in FIG. 11 in conjunction with knowledge of a reference point(s) 192 in such an interoperative scanner would enable the clinician to move the predetermined target region 44 or interoperatively determined target position 44 to a region near the reference point 187 so that the interoperative CT, MR, etc. scans will give meaningful information for its update of surgery. The use of controller system 178 coupled to couch top 11 and the coupling to other controls of the image scanner viz. couch movement/readout would follow along the discussion above in connection with the previous figures.

Also shown in FIG. 11 is head ring 194 attached to a patient's head. The head ring is similar to, for example, a CRW stereotactic head ring made by Radionics, In., Burlington, Mass., or a Mayfield headrest made by Ohio Medical, Cincinnati, Ohio. This head ring may have index markers 195, 196, and 197 on it so that its position can be tracked by the camera system C5 and therefore the position of the head known with respect to the reference point 187. Furthermore, by detecting these index markers on the head ring and also knowing the movement position of the couch top 11 from couch index markers such as 30, 31, and 32, the patient's cranial anatomy can be brought into the region of the scanner in a quantifiable way by appropriate movements of couch top 11.

As is apparent to those skilled in the art, the system and process described above may take many forms, with a multitude of variations by those skilled in the art and in accordance with the present invention. For example, many variations of the camera form, numbers, positioning, and relative calibration are possible. Various types of treatment machines such as LINACs, proton accelerators, ultrasonic machines, interventive radiofrequency devices, interventive stereotactic apparatus of all types, as well as diagnostic machines such as CT, MR, PET, ultrasound, MEG scanners can substitute as the apparatus in the above embodiments. A variety of index markers, either surface mounted, implanted, of geometric area type, skin bands, linear and geometric structures taped to the skin, and so on can be used as referencing during historic imaging and treatment or diagnostic positioning. Various process steps can be used to implement the patient target positioning and movement of the patient to bring an anatomical region into desired relationship or relative to a predetermined position or volume within the treatment or diagnostic machine.

In view of these considerations, and as will be appreciated by persons skilled in the art, implementations and systems could be considered broadly and with reference to the claims as set forth below.

What is claimed is:

1. A system for determining a location of an anatomical target with reference to a medical apparatus, which comprises:

a computer for storing and processing image scan data representing a patient's anatomy including an anatomical target, and referenced in image scan coordinates;

a camera system for obtaining camera data of the patient's anatomy and the medical apparatus, and referenced in camera coordinates;

a plurality of indexing elements mountable to the patient's anatomy and the medical apparatus, each indexing element detectable by the camera system to provide the camera data;

means associated with the computer for correlating the image scan data and the camera data and for determining a location of the anatomical target with respect to the medical apparatus; and imaging means mounted in known relation to the camera system for providing image data of the patient's anatomy, and having comparative means associated with the computer for comparing image data with reconstructed image data derived from the image scan data to thereby facilitate the positioning of the anatomical target with the apparatus.

2. The system of claim 1 wherein the comparative means is adapted to provide comparative images derived from the image data and the reconstructed image data, and including a display for displaying the comparative images.

3. The system of claim 2 wherein the imaging means includes an x-ray apparatus.

4. The system of claim 2 wherein the imaging means includes an ultrasound apparatus.

5. The system of claim 2 wherein the imaging means includes an MRI apparatus.

6. The system of claim 2 wherein the imaging means includes a video camera apparatus.

7. The system of claim 1 including means for automatically adjusting a position of the patient's anatomy to generally align the location of the anatomical target with a location of a treatment apparatus.

* * * * *